United States Patent [19]
Pellegrino et al.

[11] Patent Number: 5,729,585
[45] Date of Patent: Mar. 17, 1998

[54] AIR CROSS GRIDS FOR MAMMOGRAPHY AND METHODS FOR THEIR MANUFACTURE AND USE

[75] Inventors: Anthony J. Pellegrino, New Fairfield; Daniel N. Lyke, New Milford, both of Conn.; David P. Lieb, Lexington; Joseph A. Buturlia, West Boxford, both of Mass.; Michael P. Appleby, Charlottesville, Va.

[73] Assignee: ThermoTrex Corporation, San Diego, Calif.

[21] Appl. No.: 761,538

[22] Filed: Dec. 6, 1996

Related U.S. Application Data

[62] Division of Ser. No. 438,172, May 9, 1995, Pat. No. 5,606,589.

[51] Int. Cl.$^6$ .................................................. G21K 1/00
[52] U.S. Cl. ........................................ 378/154; 378/37
[58] Field of Search ............................ 378/154, 155, 378/37

[56] References Cited

U.S. PATENT DOCUMENTS

| | | | |
|---|---|---|---|
| 1,164,987 | 12/1915 | Bucky | 378/155 |
| 1,208,474 | 12/1916 | Caldwell | 378/154 |
| 2,133,385 | 10/1938 | Freeman | |
| 2,605,427 | 7/1952 | Delhumeau | 378/154 |
| 2,824,970 | 2/1958 | Ledin | |
| 3,665,186 | 5/1972 | Tajima | 250/62 |
| 3,717,764 | 2/1973 | Fujimura et al. | 250/80.71 R |
| 4,288,697 | 9/1981 | Albert | 250/505.1 |
| 4,340,818 | 7/1982 | Barnes | 250/509 |
| 4,414,679 | 11/1983 | Liebert et al. | 378/29 |
| 4,465,540 | 8/1984 | Albert | 156/252 |
| 4,688,242 | 8/1987 | Ema | 378/154 |
| 4,837,796 | 6/1989 | Ema | 378/154 |
| 4,951,305 | 8/1990 | Moore et al. | 378/147 |
| 4,969,176 | 11/1990 | Marinus | 378/149 |
| 5,062,129 | 10/1991 | Mulder | 378/156 |
| 5,099,134 | 3/1992 | Hase et al. | 250/5.51 |
| 5,198,680 | 3/1993 | Kurakake | 378/149 |
| 5,231,654 | 7/1993 | Kwasnick et al. | 378/147 |
| 5,231,655 | 7/1993 | Wei et al. | 378/147 |
| 5,239,568 | 8/1993 | Grenier | 378/147 |
| 5,263,075 | 11/1993 | McGann et al. | 378/147 |
| 5,291,539 | 3/1994 | Thumann et al. | 378/154 |
| 5,307,394 | 4/1994 | Sokolov | 378/34 |
| 5,357,554 | 10/1994 | Schneiderman et al. | 378/155 |
| 5,389,473 | 2/1995 | Sokolov | 430/5 |
| 5,418,833 | 5/1995 | Logan | 378/154 |
| 5,455,849 | 10/1995 | Logan et al. | 378/154 |

FOREIGN PATENT DOCUMENTS

| | | |
|---|---|---|
| 441019 | 5/1974 | U.S.S.R. |
| 760536 | 5/1980 | U.S.S.R. |

OTHER PUBLICATIONS

Ruth and Edward Brecher, The Rays, 1969, pp. 205–210, Baltimore, Md.

*Primary Examiner*—Don Wong
*Attorney, Agent, or Firm*—Ware Fressola Van Der Sluys & Adolphson

[57] ABSTRACT

Air cross grids, for absorbing scattered secondary radiation and improving X-ray imaging in general radiography and in mammography, are provided with a large plurality of open air passages extending through each grid panel. These passages are defined by two large pluralities of substantially parallel partition walls, respectively extending transverse to each other. Each grid panel is made by laminating a plurality of thin metal foil sheets photo-etched to create through openings defined by partition segments. The etched sheets are aligned and bonded to form the laminated grid panel, which is moved edgewise during the X-ray exposure to pass primary radiation through the air passages while absorbing scattered secondary radiation arriving along slanted paths.

4 Claims, 9 Drawing Sheets

AIR CROSS GRIDS FOR MAMMOGRAPHY AND METHODS FOR THEIR MANUFACTURE AND USE

This application is a division of application Ser. No. 08/438,172, filed May 9, 1995, now U.S. Pat. No. 5,606,589.

BACKGROUND OF THE INVENTION

1. Field of the Invention

The present invention generally relates to the field of medical radiography, and more particularly to a method of making an X-ray scatter reducing air cross grid for use in mammographic procedures, a movable or Bucky air cross grid produced by the method and a method for using the air cross grid in a mammographic procedure.

2. Description of the Prior Art

Scattered X-ray radiation (sometimes referred to as secondary or off-axis radiation) is generally a serious problem in the field of radiography. Scattered X-ray radiation is a particularly serious problem in the field of mammography where high contrast mammogram images are required to detect subtle changes in breast tissue.

Prior to the present invention, scattered X-ray radiation in mammography has been reduced through the use of a conventional linear focused scatter-reducing grid. The grid is interposed between the breast and the film-screen and tends to allow only the primary, information-containing radiation to pass to the film-screen while absorbing secondary or scattered radiation which contains no useful information about the breast being irradiated to produce an X-ray image.

Conventional focused grids used in mammography generally comprise a plurality of X-ray opaque lead foil slats spaced apart and held in place by aluminum or fiber interspace filler. In focused grids, each of the lead foil slats, sometimes referred to as lamellae, are inclined relative to the plane of the film so as to be aimed edgewise towards the focal spot of the X-rays emanating from the mammographic X-ray source. Usually, during a mammographic exposure, the standard practice is to move the focused grid in a lateral direction, perpendicular to the lamellae, so as to prevent the formation of a shadow pattern of grid lines on the X-ray image, which would appear if the grid were allowed to remain stationary. Such moving grids are known as Bucky grids.

One problem with conventional mammographic grids of the type described above is that the aluminum or fiber interspace filler material absorbs some of the primary, relatively low energy, information-containing X-ray radiation. Because some of the primary radiation is absorbed by the interspace material, the patient must be exposed (theoretically) to a higher dose of radiation than would be necessary if no grid were in place in order to compensate for the absorption losses imposed by the grid. It is an obvious goal in all radiography applications to expose the patient to the smallest amount of radiation needed to obtain an image having the highest image quality in terms of film blackening and contrast.

Another problem with such conventional focused mammographic grids of the parallel lamellae type described above is that they do not block scattered radiation components moving in a direction substantially parallel to the plane of the lamellae. The resulting images using these grids have less than optimal darkness and contrast.

These and other disadvantages, such as structural weaknesses, with the conventional focused scatter reducing grids of the type described above are set forth in U.S. Pat. Nos. 1,476,048; 2,133,385; and 2,605,427. Several prior art patents, such as U.S. Pat. Nos. 4,288,697; 4,465,540; 4,951,305 have suggested focused crossed-pattern type grid structures to overcome some of the above noted disadvantages with the conventional parallel-lamellae scatter reducing grids described above. For example, U.S. Pat. No. 2,605,427 suggests forming a cross-patterned grid comprising a plate of a substance permeable to X-rays formed, in two preferably perpendicular directions with narrow closely-spaced grooves filled with a substance impermeable to X-rays. The basic problem with the cross-patterned grid described in this U.S. Pat. No. 2,605,427 is that the X-ray permeable materials, similar to the fiber and aluminum interspace materials in conventional mammographic grids currently used, are not totally X-ray permeable, that is, the material still absorbs some of the primary X-rays, resulting in a lower transmission rate of primary X-rays to the X-ray film and leading to higher X-ray dosages to the patient.

U.S. Pat. No. 4,465,540 describes a collimator for a Gamma camera system. The collimator described therein is constructed by assembling a plurality of X-ray collimating layers comprising radiation-absorbent materials having openings etched therein. The collimating layers are assembled in a spaced apart relationship with a plurality of radiation transmissive spacer layers between each collimating layer. The assembly is held together at the periphery by bolts. Several problems arise when attempting to apply this particular construction to make a focused, moving mammographic scatter reducing grid. First, like other grids previously mentioned, there are several layers of X-ray transmissive spacer layers within each focused passage or opening. Although characterized as X-ray transmissive, these layers within the X-ray transmissive openings still absorb more radiation than if the openings were straight through and only filled with air. These layers also present the potential to cause some scatter of X-rays leaving the collimator. Another problem with this construction is that the X-ray absorbing layers in the middle of the collimator are not physically bound together. Although not apparently a problem in Gamma camera systems, this can present a problem in mammography because the common practice is to move the grid during an exposure to blur grid lines, and there is a risk that the unbonded layers could physically separate from one another and distort the resulting image.

Two additional patents, U.S. Pat. Nos. 5,231,654 and 5,231,655, describe computerized tomography (CT) X-ray collimators formed of one or more layers of Corning Fotoform™ photosensitive glass, with focused passages etched away to form cross grids with thick glass partitions between the air passages. The effective primary radiation-transmission area of these cross grids is drastically reduced by the radiation absorbing cross-sectional area of the thick glass partitions. Only about 20% to 25% of the grid transmits primary radiation and the X-ray dose absorbed by the patient is correspondingly increased. Therefore, such thick-partition glass grids are totally unsuitable for low energy mammography X-rays requiring maximum image contrast with minimum radiation dosage.

SUMMARY OF THE INVENTION

Accordingly, a principal object of the present invention is to produce sturdy cellular air cross grids having focused air passages extending through them offering maximum radiation transmissivity area and minimum structural area necessarily blocking primary radiation while maintaining adequate structural integrity for the cross grid during use.

Another object of the invention is to provide such air cross grids maximizing contrast and accuracy of the resulting mammograms produced with the same or comparable radiation dosages.

A further object of the invention is to provide such cross grids sturdily formed of laminated layers of metal selectively etched by chemical milling or photo-etching techniques to provide open focused passages through the laminated stack of etched metal layers.

Still another object of the invention is to provide methods of fabricating laminated focused metal cross grids of this character, employing adhesive or diffusion bonding joining the abutting edges of thin partition portions of the laminated abutting layers with minimum intrusion of bonding material into the open focused passages.

Other objects of the invention will in part be obvious and will in part appear hereinafter.

The invention accordingly comprises the features of construction, combinations of elements, and arrangements of parts which will be exemplified in the construction hereinafter set forth, and the scope of the invention will be indicated in the claims.

THE DRAWINGS

For a fuller understanding of the nature and objects of the invention, reference should be made to the following detailed description taken in connection with the accompanying drawings, in which.

BEST MODE FOR CARRYING OUT THE INVENTION

Figure 1:
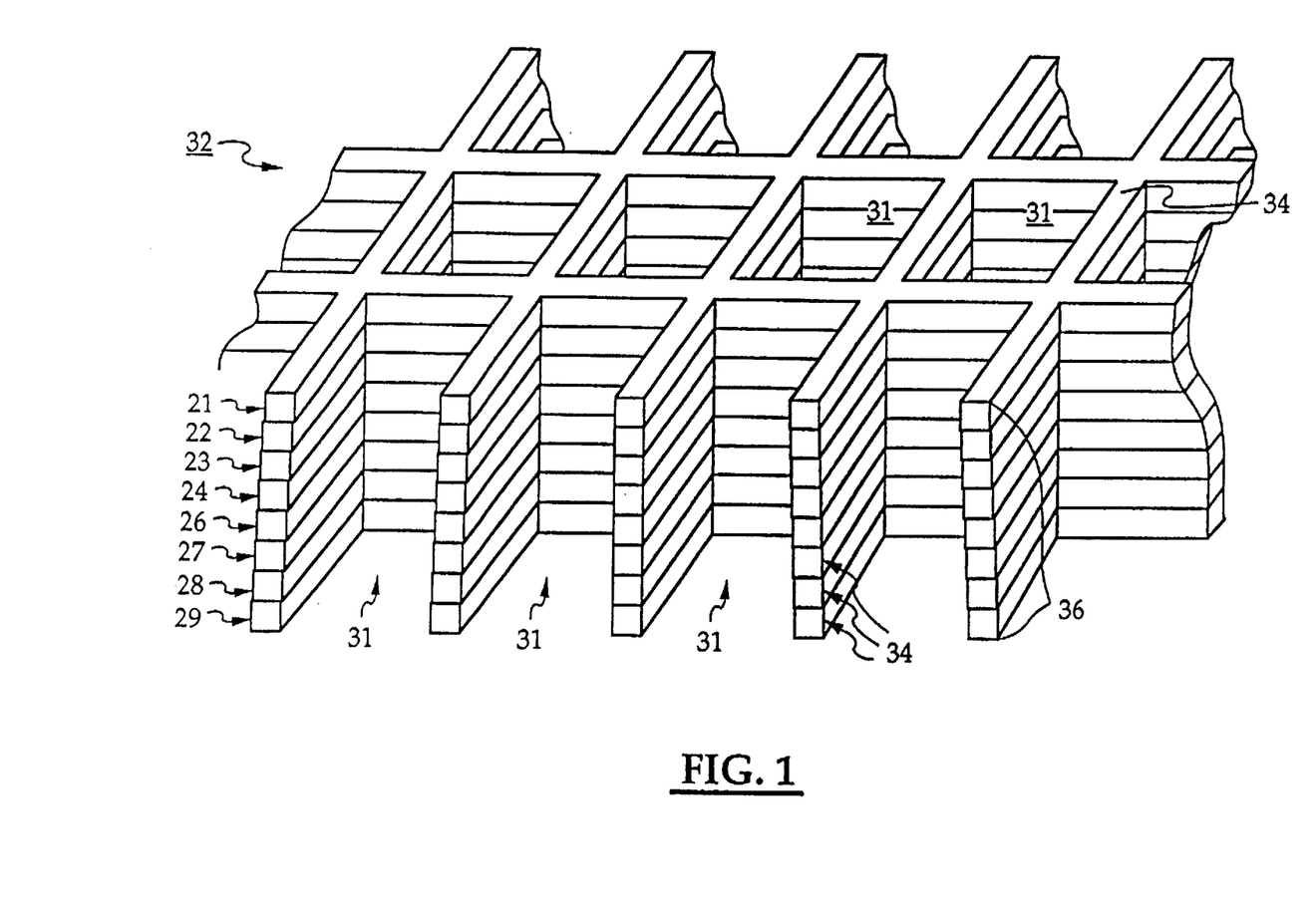
FIG. 1 is a fragmentary enlarged perspective view of a portion of a focused laminated metal layer air grid of this invention with the angle of convergence between adjacent air passages being exaggerated to illustrate the focused character of the grid.

The fragmentary perspective view of FIG. 1 illustrates a cellular air cross grid typical of the grids of the present invention with the partition walls defining the cells passing through the grid being shown with an exaggerated convergence angle between adjacent walls to emphasize the fact that the cells are focused, i.e. aligned with their central axes converging at a point corresponding to the focal source of the X-rays produced by an X-ray tube in a mammography X-ray unit for example. These air passages or cells are unobstructed by any transverse interleaved layers of plastic or metal, and no surface covering layers of protective sheet material are needed with the air cross grids of the present invention.

Figure 2:
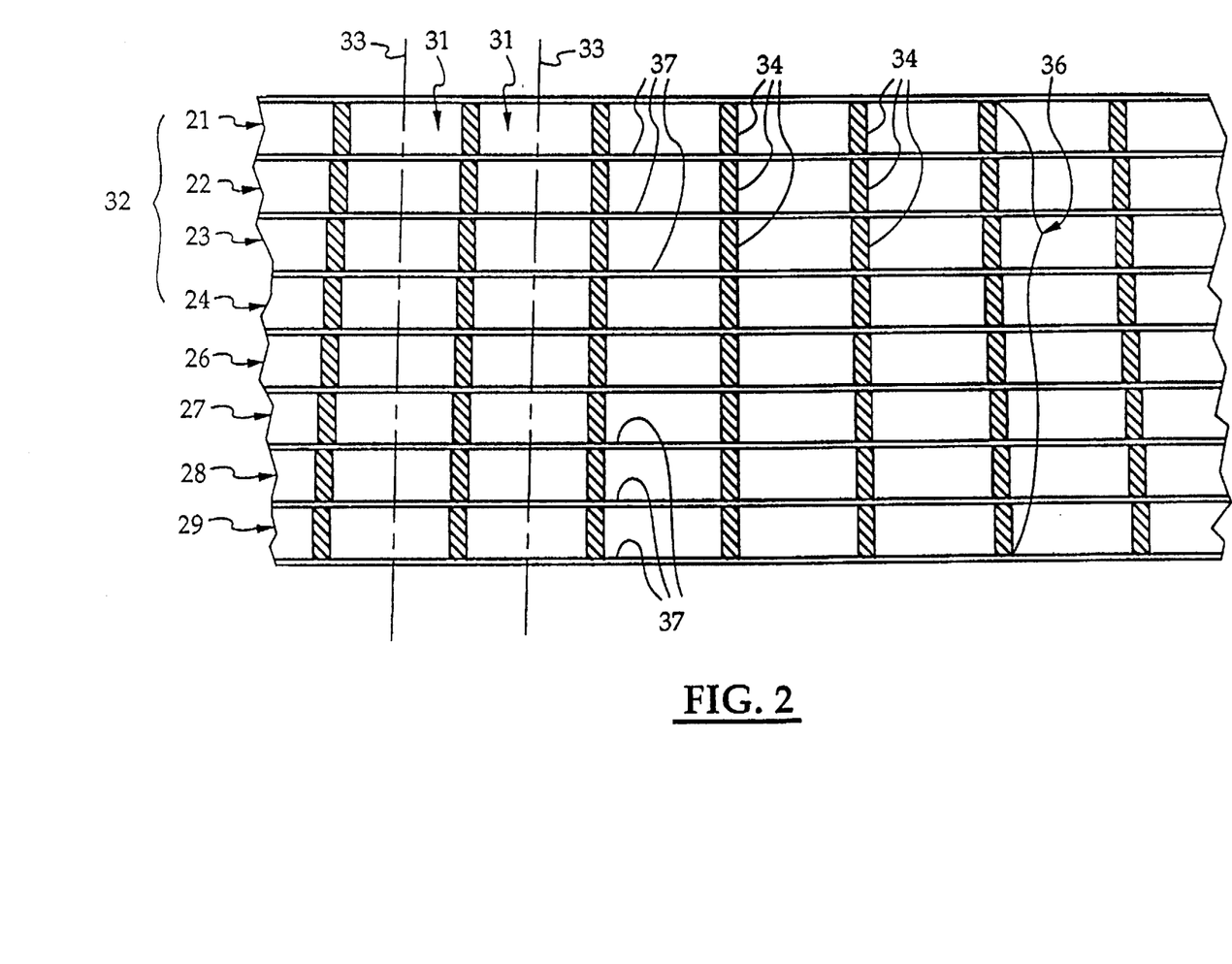
FIG. 2 is a further enlarged cross-sectional side elevation view of the cross grid shown in FIG. 1, taken along the line 2—2 shown in FIG. 5.

As shown in FIGS. 1 and 2, these cross grids are formed of stacked layers of metallic foil sheet, preferably beryllium-copper alloy or brass. Aligned portions of each sheet are removed by chemical milling or photo- etching to create the open air cell portions of each sheet, separated only by the partition wall portions thereof formed in a cross grid pattern. These chemically milled metal layers are then bonded together in the stacked configurations illustrated in FIGS. 1 and 2 where the convergent focussing orientation of the radiation axes forming the center line of each air passage or cell are easily seen to be converging at a focal point above the cross grids shown in these figures.

The general proportions of the chemically milled metallic sheets and the dimensions of the partition wall portions thereof and the air cell passageways formed therethrough are best seen in FIGS. 1, 2, 5 and 14, which are intended to illustrate the very large volume of air cells extending entirely through the cross grids of the present invention, as contrasted with the very thin partition walls between the air cells formed by the portion of these metal sheets remaining after the photo etching process is completed on each sheet.

Figure 5:
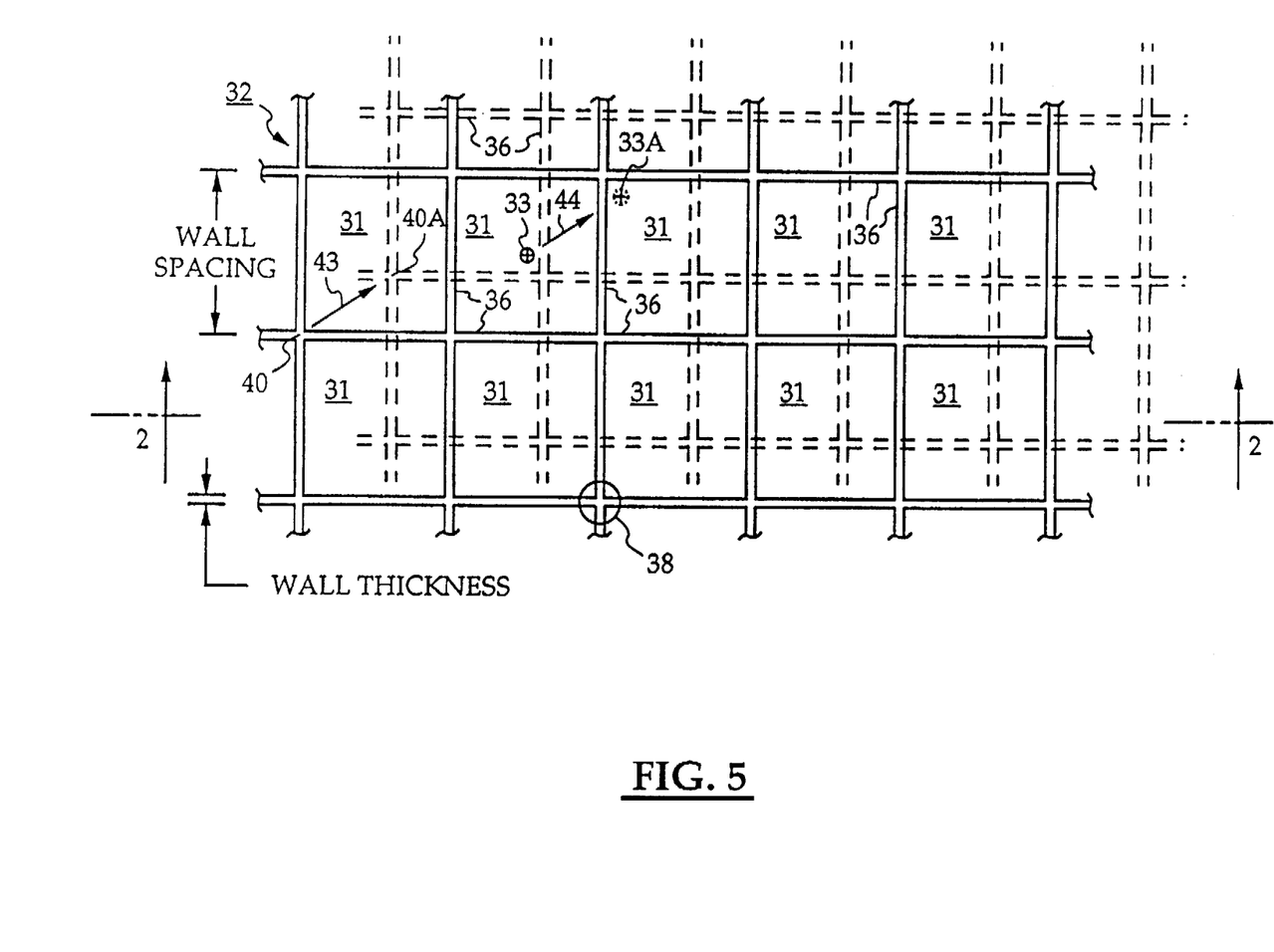
FIG. 5 is a fragmentary top plan view of the air cross grid shown in FIGS. 1 and 2 illustrating a typical translation movement direction of the air cross grid during the X-ray exposure.
Figure 10:
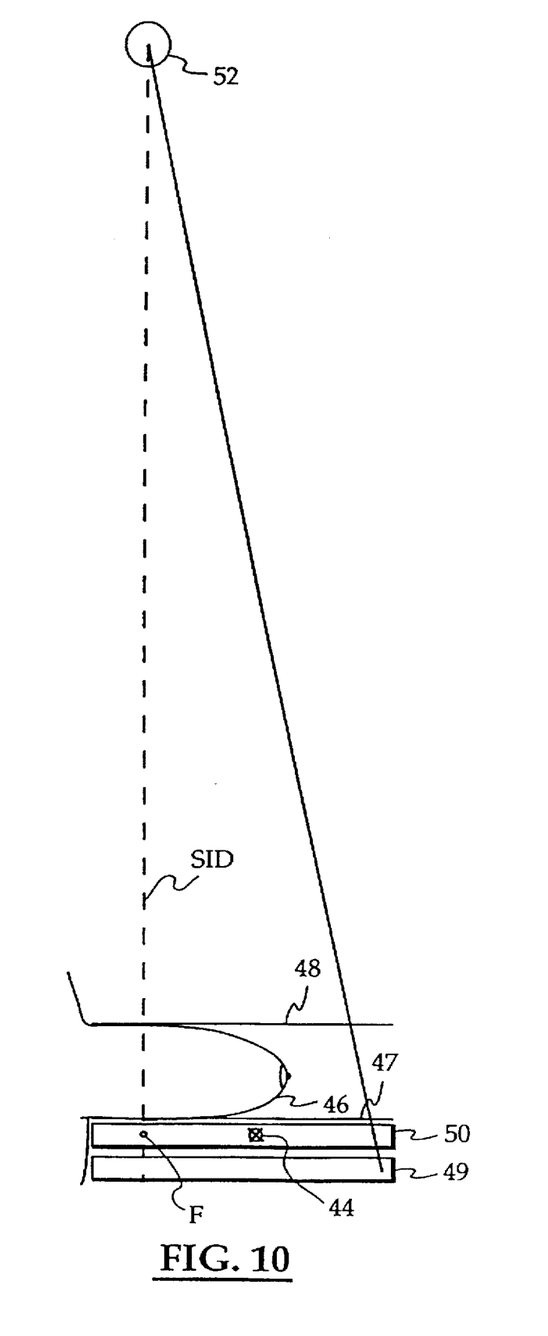
FIG. 10 is a schematic side elevation diagram showing the radiation focal source of the X-ray tube delivering radiation to the patient's compressed breast beyond which is an air grid of the present invention and the photographic plate or image receiver.
Figure 11:
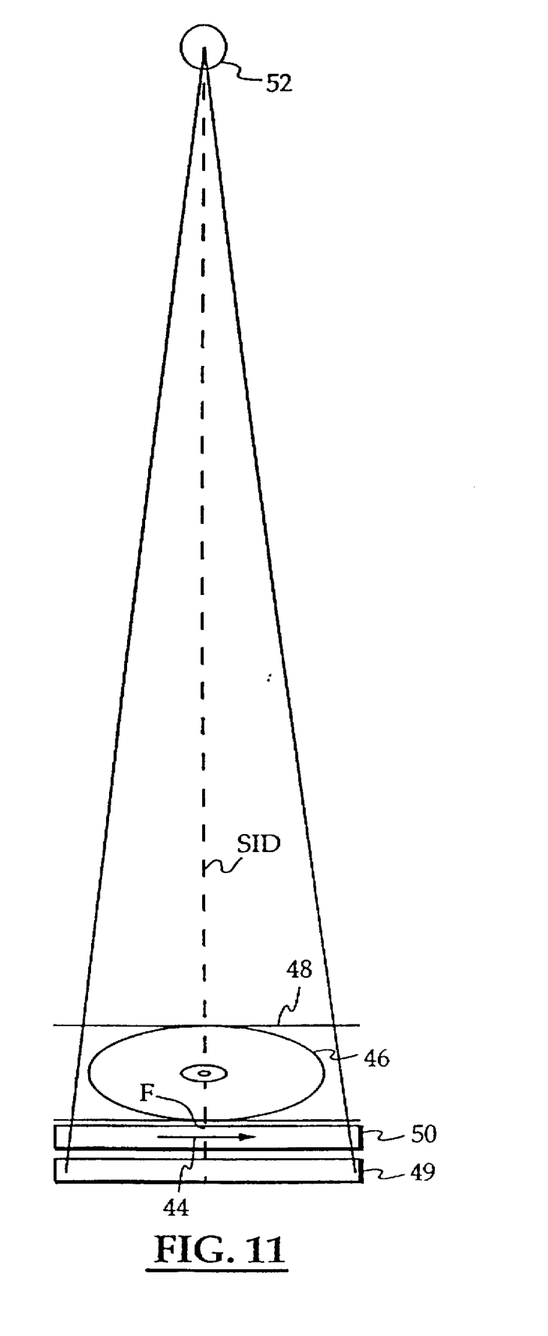
FIG. 11 is a corresponding front elevation diagram corresponding to FIG. 10.

Thus in FIGS. 1, 2 and 5 it will be seen that the stack of eight sheets 21, 22, 23, 24, 26, 27, 28 and 29 are assembled and laminated together to define the large plurality of open air cell passages 31. These passages 31 all pass through the entire depth of the assembled laminated multi-layer grid assembly 32, and each air cell passage 31 may be considered to have a central axis 33 defining the direction it extends through the cross grid assembly 32. As indicated in FIGS. 2, 10 and 11, these axes 33 for adjacent cells 31 preferably converge at a focal point 52 corresponding to the source of the X-rays delivered through this grid 32.

The partition walls defining and separating the adjacent air cells 31 are formed of individual partition segments 34 which are the only part of the metal foil sheet remaining after the chemical milling operation has removed the air cell portions thereof, aligned to create the through air cell passageways 31. These partition segments 34 are thus aligned with each other in successive sheets of the laminated assembly, as shown in FIGS. 1 and 2, to create partitions or sidewalls 36 shown at the right hand sides of FIGS. 1 and 2. The width of these partition segments 34 forming the sidewalls 36 measured in the plane of each metal sheet lamination is preferably between 0.0010 inches and 0.0020 inches, and in a preferred embodiment a partition width or wall thickness of 0.0012±0.00015 inches. The resulting grid structure 32 is a sturdy and highly useful implement in the mammography field, and provides the desired absorption of scattered secondary radiation entering the air cell passages 31 at a considerable angle from the axes 33. As a result, when from 8 to 20 or more layers of the cross grid laminations 21, 22 etc. are bonded together in the laminated assembly 32, this cellular air grid is unusually well adapted to perform its scatter-reducing function while transmitting substantially all of the desired primary radiation without attenuation, significantly improving mammogram contrast and image quality at comparable radiation dosages.

The beryllium-copper foil sheet material employed to form the laminations of 21, 22, 23 etc. is referably about 0.004 inches thick, and is preferably formed of a layer of beryllium-copper alloy known as Alloy No. 190, having a temper specified as "XHMS", sold by Brush Wellman of Fairfield, N.J.

The air cell openings formed by photo-etching between the partition segments 34 in each lamination may be from 0.010 inches to 0.030 inches in internal width. Center to center distances between the center lines of the partition segments 34 forming the walls defining each air cell, have been selected as 0.017 inches in a preferred embodiment of the cellular air grids of the present invention illustrated in the figures, as shown in FIG. 5, where the thickness of the partition walls 34 is shown to be 0.0012 inches, falling within the range of 0.0010 inches to 0.0020 inches in useful embodiments of the device. With these dimensions as illustrated in FIG. 5, the very large volume of the overall assembly 32 occupied by air cell passages 31 is evident, as compared to the very small volume of the overall assembly 32 occupied by the partition walls 36. For these dimensions, the partition walls occupy only about 14% of the total surface area of this air cross grid 32, leaving 86% of the total cross-sectional area available to receive and transmit the desired information-bearing primary radiation directly to the imaging unit, the X-ray film or digital imaging device. A cross grid 32 having these dimensions actually achieves transmission of about 82% of the desired primary radiation, while substantially blocking scattered secondary radiation. This effectiveness is considerably greater than has ever been achieved by any other form of commercially available fixed or moving grid. While a total number of eight laminations are illustrated in the figures, as many as 18 or 20 or more laminations may be employed if desired. To simplify the fabrication process, the minimum number of laminations required to achieve the desired scatter reduction is customarily employed.

The bonding of the sheet metal foil layers 21, 22, 23 etc. together to form the laminated assembly 32 may be achieved by brazing, soldering, diffusion bonding or adhesive bonding techniques. It has been found that adhesive bonding with 3M adhesive coatings produced by Minnesota Mining and Manufacturing Company ("3M") have produced highly effective air cross grid assemblies 32, using the techniques hereinafter described for the fabrication assembly methods. These methods apply a thin coating of epoxy adhesive 37 to the surfaces of the partition segments 34 and particularly to those portions of the surface planes of the metal foil sheets which are juxtaposed in abutting contact as the chemically milled layers are laminated together. These production methods also eliminate almost all excess adhesive which might otherwise project into air passages 32, and might reduce the size of these air cell passages.

An alternate fabrication method employs a thin plated coating of lead, lead-tin or other metal on the partition segments, which are stacked in accurate registration, clamped together under pressure, and heated to melt and fuse the plated coatings, bonding all of the stacked layers to form an integral laminated air grid.

Figure 6:
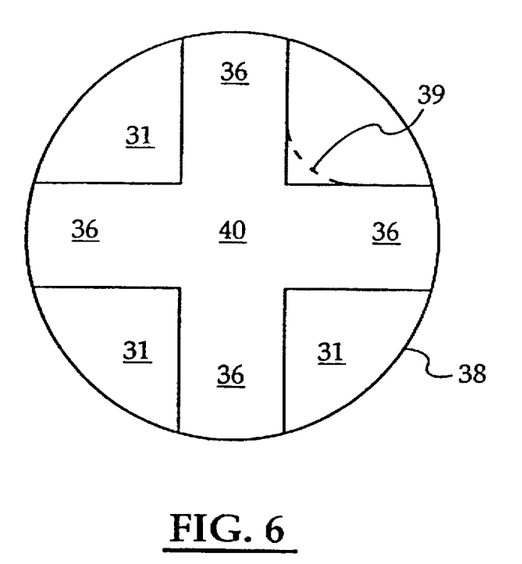
FIG. 6 is a fragmentary greatly enlarged top plan view of a photoresist mask pattern forming the intersection of two crossed partitions illustrated in the fragmentary plan view of FIG. 5.

In the plan view of FIG. 5 showing an enlarged portion of the air cross grid 32 of the present invention, the air cell passages 31 and the partition walls 36 defining them are clearly illustrated. In the lower portion of FIG. 5 is a circle 38 identifying a corner junction where perpendicular partition walls 36 join, and the photoresist pattern forming such junctions is illustrated in enlarged detail in FIG. 6. In this figure, a possible problem sometimes encountered with the chemical milling or photo etching process is also illustrated by a dashed line 39 showing a corner fillet which may be formed at the junction 40 where the partition walls 36 join. Such a fillet 39 is undesirable because it reduces the overall area of the air grid cell 31 available for passing primary radiation, and it increases the cross sectional area of the junction regions, which are carefully dimensioned for optimum elimination of image shadows by grid movement during each X-ray exposure. In order to reduce the likelihood that such fillet 39 will appear, the mask or masking tool employed in the chemical milling or photo-etching process is preferably provided with square cornered diagonal projections 41, reducing the effective cross-sectional area of the junction regions to the desired value.

Figure 7:
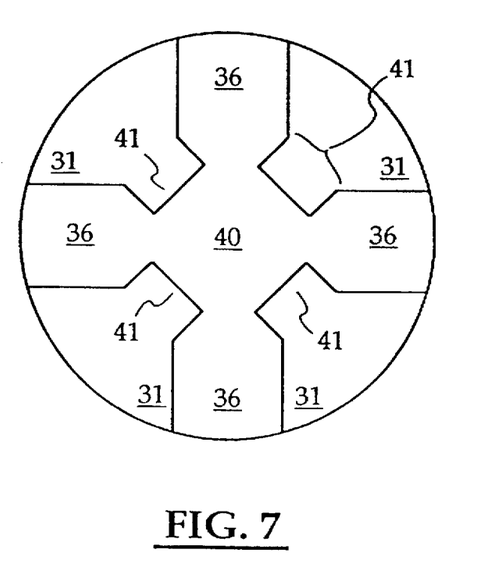
FIG. 7 is a view corresponding to FIG. 6 showing a modified photoresist mask pattern incorporating axial grooves and employed to form the intersection of two crossed partitions in a different version of the invention, reducing any rounded filleting which otherwise might occur at the intersection.

Diagonal projections 41 protrude into the junction area 40 from each of the four air cell passage regions 31 surrounding junction 40, all as illustrated in FIG. 7. Projection 41 has the effect of ensuring that any "filleting" left behind by the chemical milling process will be concentrated at the inside corners of the resulting diagonal groove, leaving substantially the entire square area of each air cell passage region 31 open directly to its corner at each junction 40, and reducing the junction area to the desired value.

Figure 8:
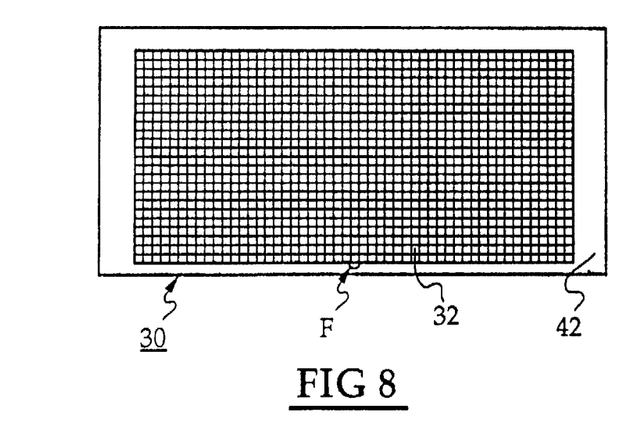
FIGS. 8 and 9 are top plan views of the assembled grids of the present invention with the focal point shown in the center of the lower edge thereof. The cross partitions of the grid of FIG. 8 are parallel to its edges, while the cross partitions shown in the grid of FIG. 9 are inclined at an angle permitting the sideways translation of the grid itself to produce the diagonal translation movement indicated in FIG. 5.
Figure 9:
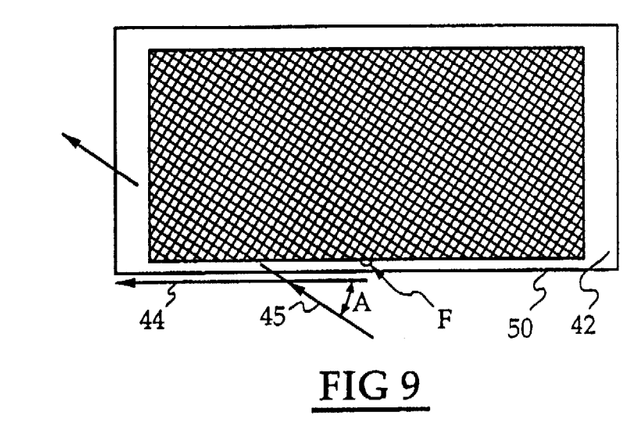

FIGS. 8 and 9 show the general appearance of the cellular air cross grids of the present invention with the outer edges mounted in protective frames 42. In FIG. 8 the pattern of partitions 34 and cells 31 is aligned with the rectangular edges of the frame 42. Also shown in FIG. 8 is a point F midway along the lower longer edge of the cross grid at the frame, close to the patient's chest wall for mammography, and this is the joint designed to be positioned directly under the focal source point 52 of the X-rays delivered through the grid, as will be explained more fully with regard to FIGS. 10 and 11. For general radiography, the focal point F is normally placed in the center of the grid panel, and not near one edge. The air cell passages 31 close to this point F will have their cell axes 33 substantially parallel to the perpendicular axis of the cell directly at point F. As the observer examines cells further away from point F, the cell axes 33 of such cells will be seen to be progressively more slanting, to converge at the same focal point 52 directly above point F when the cross grid is in use. This successively greater converging slant of the axes 33 is illustrated in FIG. 2, somewhat exaggerated for clarity.

When the cross grids of the present invention are used as moving or Bucky grids, provided with translation movement during the X-ray exposure, the effect is to avoid any shadow image of the partition walls 36 which might be created if the cross grid remained in a stationary position during the exposure. FIG. 9 shows a diagonal orientation of the partition walls 36 and the air cell passages 31 when the assembly 32 is mounted in a frame 42 for use as a moving or Bucky grid. By examining FIG. 5 with reference to FIG. 8 and FIG. 9, it will be evident that movement of the cross grid in the normal lateral direction, parallel to the long edge of frame 42 in which the focal point F is positioned—the normal translation movement direction for a moving or Bucky grid—would avoid shadow images of the partitions 36 shown as vertical partitions in FIG. 5, but would result in the horizontal partitions 36 of FIG. 5 moving edgewise, maintaining their same position and leaving a shadow on the X-ray image. Any such shadow is undesired and the purpose of using a moving or Bucky grid is to avoid any such shadows of lamellae or partitions in the grid which are required to absorb scattered radiation. Such shadow images would degrade the resulting X-ray image and might conceal calcifications or extremely small dots having important significance in mammography. Radiologists specializing in mammography generally recommend using Bucky grids to avoid any such shadow images, in order to produce the most detailed images possible. To avoid the edgewise translation movement which might leave such an image of a partition wall, the diagonal arrangement of the partition walls 36 and air cell passages 31 illustrated in FIG. 9 is preferred. This orientation produces the diagonal movement indicated in FIG. 5 from the full line position of the partitions 36 to the dotted line positions of partitions 36, in the direction of the arrows 43 and 44.

Arrow 43 at the left hand side of FIG. 5 shows the direction of movement of a particular junction 40 to its new position 40A during the course of the translation movement. Arrow 44 shows the translation of a central axis 33 of one of the air cell passages 31 to its new position 33A following translation movement.

These relative positions illustrated in FIG. 5 are examples of instantaneous intermediate positions in which the cross grid structure will be found at various times during its continuous diagonal translation movement during the entire X-ray exposure period. This is desired to avoid even the shadow image which might be created if the partition walls came to a stop at any time during the exposure either to reverse direction or to continue after an increment of movement. Continuous movement during exposure thus produces the most effective elimination of all such shadow images from the partition walls of a moving grid. The direction of movement for such a moving or Bucky grid as that shown in FIG. 9 is indicated in the schematic diagrams of FIGS. 10 and 11.

FIG. 10 is a side view of a mammography X-ray procedure showing the patient's breast 46 held stable in the mammography device between an underlying breast tray 47 and an overlying clamping plate 48 gently moved into position to deter any unnecessary movement during the exposure and to minimize the thickness of breast tissue for best X-ray imaging. The imaging unit beneath the breast tray 47 includes the moving Bucky grid 50 of the kind illustrated in FIG. 9 with diagonal orientation of the cross grid pattern, overlying a film cassette 49 incorporating the X-ray film 51 encased inside cassette 49.

Point F is indicated at the left-hand edge of grid 50 close to the patient and directly beneath the focal source point 52 which is shown with a source to image distance or SID represented as a dash line extending from X-ray source 52 through the patient's breast 46 and through the Bucky grid 50 at point F into the film cassette 49 to expose the film 51. The SID dash line is perpendicular to the Bucky grid 50 and to the film 51 as indicated by the diagram of FIG. 10. The direction of movement of Bucky grid 50 is indicated by an X shown midway across the shorter dimension of Bucky grid 50 from the patient to the outer free edge of the Bucky grid, thus indicating that the grid moves in the direction parallel to the patient's sternum, from right to left for example.

The front elevation diagram of FIG. 11 further indicates the normal positioning of the air cross grid 50 of the present invention, when used as moving or Bucky grid, moving from the patient's right to the patient's left in the direction shown by the arrow 44 during the X-ray exposure. Here it is indicated that the point F is positioned under the middle of the breast at the midpoint of the translation movement of the Bucky grid during the exposure period. The SID dash line extending from X-ray source 52 directly perpendicular to film cassette 49 containing film 51 identifies the radiation travelling directly along this perpendicular radiation axis as it passes through Bucky grid 50 at point F and travels toward the film 51 in cassette 49.

The actual dimensions of a preferred version of the movable Bucky grid 50 are 18 centimeters in width and 26 centimeters in length for an 18 cm×24 cm cassette, or 24 cm×32 cm for a 24 cm×30 cm cassette, and the SID distance from the X-ray film image to the X-ray source is 63 centimeters. The grids of this invention are preferably moved at a precise angle and distance during the X-ray exposure so that an integral number of grid lines in each of the two perpendicular partition directions will pass each point of the image. In addition, the ratio of the two directions is preferably set so that there is no repeating trace pattern of the intersections of grid partitions until at least 9 grid lines have passed a specific image point.

Cross-Grids

Cross grid partitions absorb scattered X-rays slanting in many directions. To eliminate imaging grid lines, the X-ray intensity variations produced by moving the grid should be reduced below about 1%. The usual technique with fine linear (non-cross) grids is to have the grid move with uniform velocity during the exposure. If the motion is fast enough so that about 100 lines cross each spot, the absorption difference due to the start and end positions during the exposure will be less than one line crossing or 1%.

With cross grids the patterns are coarser, and the grid must be angled so that the motion translates both of the sets of perpendicular lines. Because the grid intersections represent a single line width, these areas will tend to be overexposed as compared to the inbetween or open areas which are traversed by the two sets of cross lines. By choosing the grid translation angle so that as many intersection traces as possible are adjacent rather than coincident, the intersection traces can cover the entire space and become invisible.

Thus there are two components to be optimized in the motion for the cross grid, first a linear transverse motion such that the grid lines uniformly cover the space, and second an angle, or diagonal motion such that the image-traces of all intersections of the cross lines cover as much area as possible, without trace overlaps.

In order to achieve the X-ray exposure time required to produce a mammogram having optimum image quality during X-ray grid panel translation, the following steps are recommended: making a brief test exposure while measuring the X-ray transmission value of the breast to be imaged, determining from said transmission value the total X-ray exposure time require for optimal imaging, and exposing the patient to X-rays for said total X-ray exposure time so determined while imparting edgewise translation movement to said grid panel. If desired, the total X-ray exposure time so determined to be required for optimal imaging can be divided into two increments, separated by a pause, with the grid panel translation movement occurring at uniform velocity through each increment of exposure, but with the direction of grid panel movement being reversed during the second increment of exposure, whereby deceleration, stopping and reversed acceleration of the grid panel all occur during the pause between the increments of X-ray exposure.

A suitable linear transverse motion would move the grid lines exactly one open space distance with uniform velocity during the exposure. Then each portion of the image will be obscured for exactly the same interval, and there will be no line image. For the cross lines to behave similarly the grid must be angled such that an integral number of lines will be moved in both sets. Thus angles giving line motion ratios of 1:1, 1:2, 5:4 etc. would be suitable. The more lines that are moved, the more tolerance allowed in the position, since any fixed error in the mechanism will be a smaller fraction of the total motion. The maximum travel is limited by both the focus shift and the constraints of the Bucky stage. A practical limit for travel is about 2.5 cm. With a 1 mm grid spacing and a 45 degree angle, the motion can cover about 18 lines.

The angle of the grid determines the repeat pattern of the image-traces of intersections and to cover the space as uniformly as possible the number of lines to a repeat should be large. Ratios such as 9:1, 9:2:—9:8 appear to give adequate coverage. About 16:11 (34.6°) is a suitable angle (FIG. 9). Two patterns then are 16 lines by 11 lines.

Fabrication Methods

The air cross grid 30 and the moving Bucky grid 50 shown in FIGS. 8 and 9, both incorporating the cross grid structure illustrated in FIGS. 1, 2 and 5, may be fabricated using the choice of bonding techniques previously mentioned for joining the stacked layers of chemically milled beryllium copper foil sheet in the desired registration, with the openings therein forming the air cell passages 31 illustrated in the figures. These techniques include brazing, soldering, diffusion bonding or adhesive bonding.

Adhesive Bonding

Figure 13:
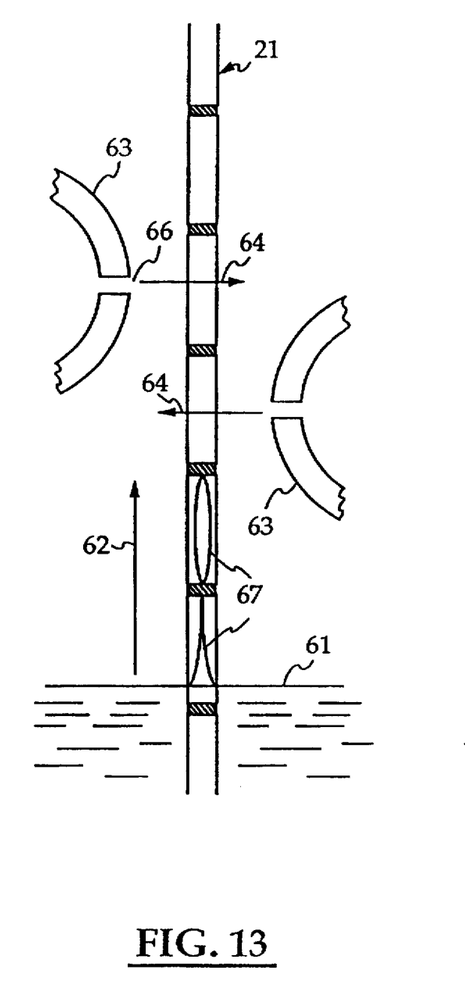
FIG. 13 is an enlarged end elevation view of a layer already photo-etched to produce air passages therethrough between crossed partitions, which is being lifted edgewise from an adhesive dipping bath between a pair of air knives positioned to clear away any adhesive which might be extending into the air passage.
Figure 14:
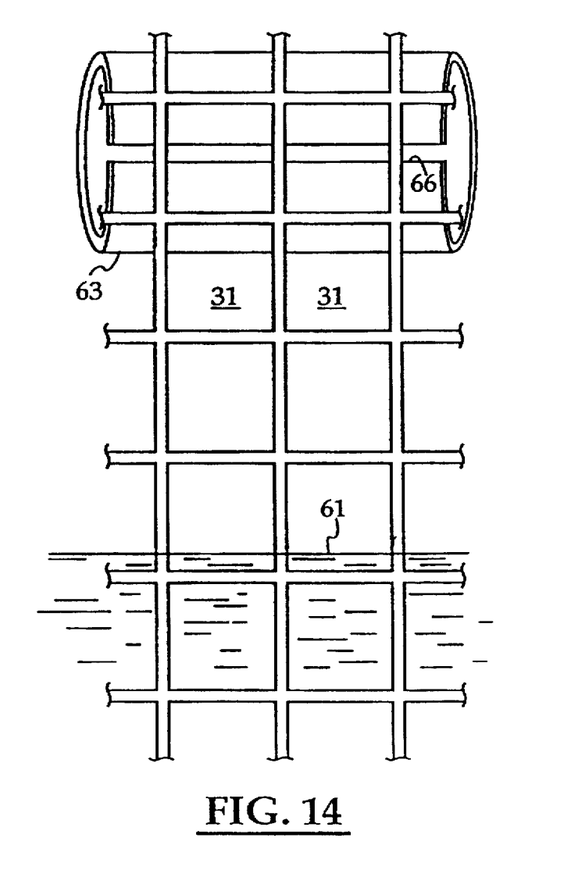
FIG. 14 is a fragmentary front elevation view corresponding to FIG. 13 showing the same lamination being drawn upward from its adhesive dipping bath, ascending past one of the air knives shown in FIG. 13.

It has been found that an adhesive dip bath coupled with air knife removal of excess liquid adhesive provides a highly workable fabrication technique in the production of these air cross grids. This production step is illustrated in FIGS. 13 and 14.

Figure 12:
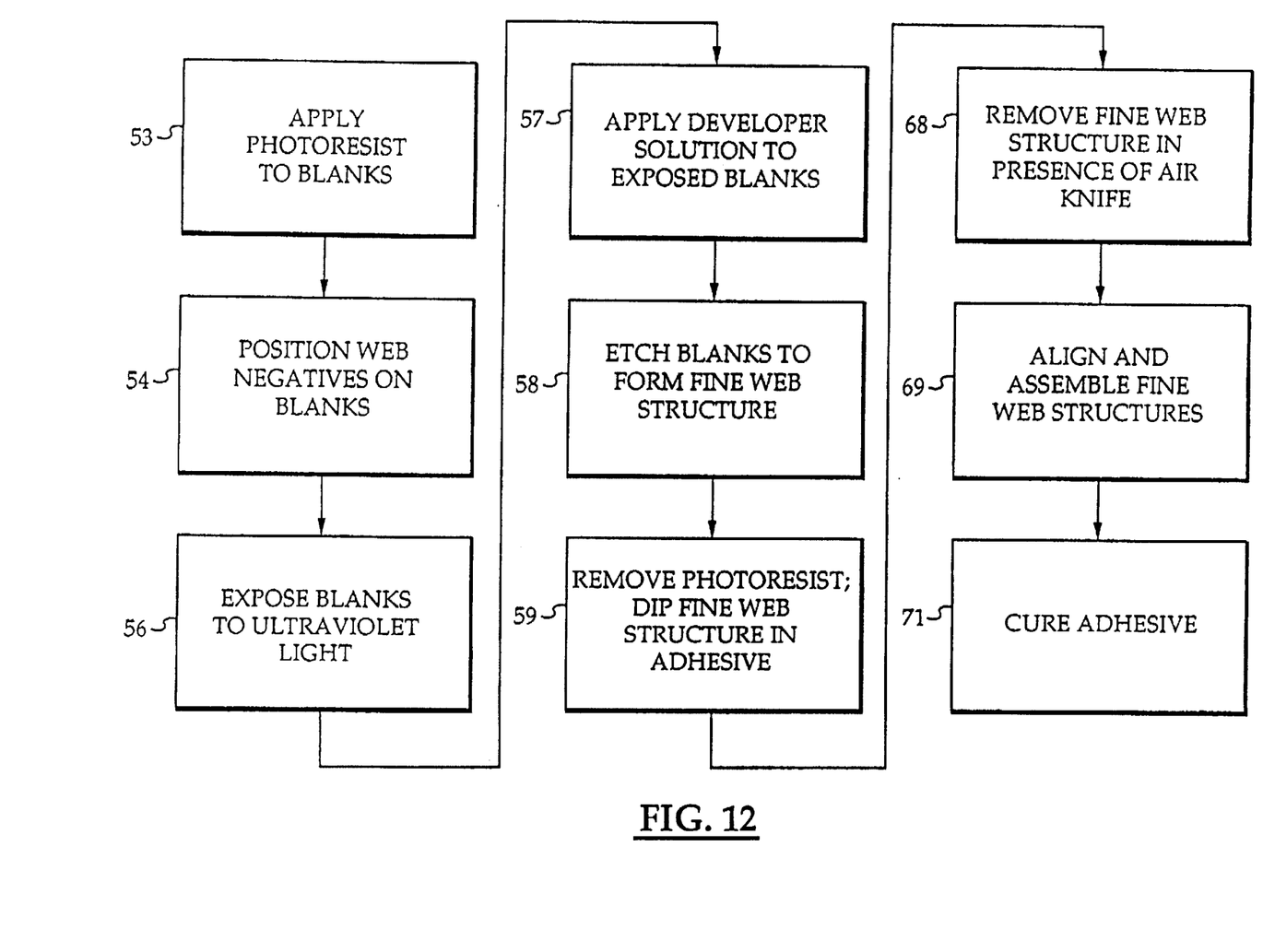
FIG. 12 is a block diagram of a first fabrication method employed to produce focused air cross grids of the present invention incorporating numerous photo-etched and laminated metal layers, bonded by adhesive.

The overall method employed to produce the adhesive-bonded air cross grids of this invention are summarized in the flow diagram of FIG. 12. Each of the multiple layers of metallic foil sheet material is first chemically milled to remove the air cell passage portions 31, leaving only the partition segments 34 in place. For this purpose, a mask tool is employed and for each metal foil layer a pair of mask tools or web negatives are applied to the opposite faces of the foil sheet material, which has been coated by a photoresist on each of its surfaces. The photoresist application step is identified as step 53 in FIG. 12 and the application of the aligned mask tools or web negatives positioned in registration on opposite surfaces of the foil sheet is identified as step 54.

Figure 4:
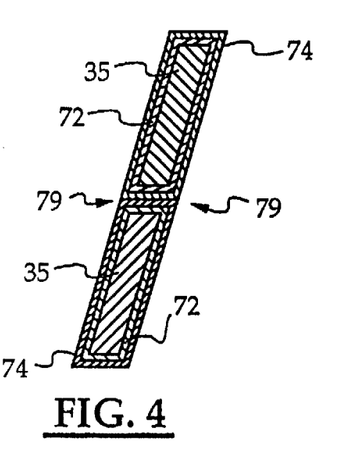
FIG. 4 is a view corresponding to FIG. 3 showing a modified embodiment of the structure.
Figure 4A:
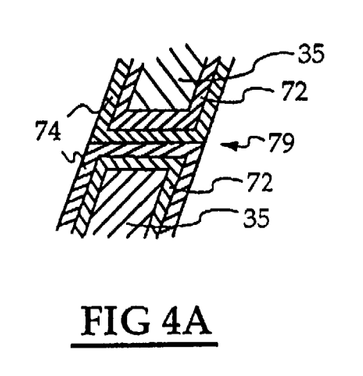
FIG. 4A is a fragmentary further enlarged side cross-sectional view of a portion of the structure shown in FIG. 4.

Identical mask tools applied to both surfaces of the metal foil will produce partition segments 34 photo-etched in planes perpendicular to the foil surface. A mask tool sized for the slightly wider "focused" spacing of the next adjacent foil sheet will produce converging "focused" partition segments 35 (FIGS. 4 and 4A).

The sandwich of two web negative mask tools aligned in registration flanking both faces of the sheet of the foil sheet blank is next exposed to ultraviolet light projected on both surfaces through the web negatives to expose the photoresist coatings to ultraviolet radiation in step 56.

The web negatives are then removed and a developer solution is applied in step 57. The foil sheet blanks are next etched in step 58 to perform the "chemical milling" removal of the air space sections 31 forming the air cell passages, leaving only the cross grid partition segments 34 as illustrated in FIG. 14.

This cross grid structure formed only of partition segments 34 is referred to as a fine web structure, and after all remaining photoresist is removed, this web is next dipped in liquid adhesive in the step 59. The liquid adhesive bath 61 is illustrated in FIGS. 13 and 14, where the web is being removed edgewise in an upward movement illustrated by the arrow 62 in FIG. 13. The upward movement of the web identified as metal sheet 21 in FIGS. 13 and 14 passes it upward between a pair of air knives 63, delivering thin wide fast moving curtains 64 of compressed air or nitrogen through an elongated narrow slot 66 formed in each of the air knives 63. These wide flat streams of compressed gas are directed diagonally at the two faces of the web structure of sheet 21, as indicated in FIG. 13, removing any bubble or film 67 of liquid adhesive which might be carried upward on the ascending web, spanning some of its passages 31 as shown in FIG. 13, for example. All such bubbles and films of adhesive are blasted from the surfaces and from spaces 31 in the ascending web structure by the action of the compressed gas stream 64 from air knives 63 and the displaced liquid adhesive thereby removed from the web structure drains back into the liquid adhesive bath 61 below.

This leaves a sufficient thin coating of liquid adhesive on each of the parallel faces of the web structure sheet 21, these being the surfaces ready for abutting engagement and aligned registration with the next sheet of metal foil being fabricated and dipped in liquid adhesive to form the succeeding sheet 22. A small quantity of liquid adhesive may adhere to the internal wall surfaces of partition segments 34. Such a small amount of liquid adhesive cures during the assembly process and does not intrude significantly into the spaces 31 of the assembled cross grid 32.

This air knife adhesive removal step is identified by the number 68 in FIG. 12 and the assembly of the successive layers 21, 22, 23 etc. aligned by registration indicia on the edge of each layer, to form the laminated assembled air grid 32 illustrated in FIGS. 1 and 2, is identified as step 69 in FIG. 12.

The preferred bonding adhesive used in these fabrication methods is 3M SCOTCH-GRIP® plastic adhesive Model 1099L, diluted with acetone in accordance with the manufacturer's recommendations to decrease its viscosity. This adhesive is air curable, requiring no heat to be supplied during curing. Another suitable adhesive is Beacon Chemical Company's MAGNA-TAC® Model E645 two part epoxy adhesive, diluted with a 50—50 mixture of acetone and isopropyl alcohol for reduced viscosity.

Figure 3:
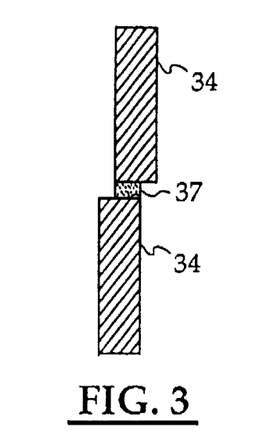
FIG. 3 is a greatly enlarged fragmentary cross-sectional side view of the partitions illustrated in FIG. 2, showing the abutting contact between the lower end of an upper partition and the upper end of a lower partition juxtaposed to form a continuous focused partition defining a focused air passage through the grid.

The curing of the adhesive between the layers identified as step 71 in FIG. 12 is performed while these layers are maintained in precise registration in the alignment illustrated in FIGS. 1, 2 and 3 to create the desired convergence of the axes 33 and provide a focused cross grid with all of these axes 33 converging at the X-ray source 52 illustrated in FIGS. 10 and 11.

If identical web negative mask tools are employed on both faces of the foil sheet material being treated by the fabrication method described with reference to FIG. 12, as previously noted partition segments result which are perpendicular to the parallel faces of each of the foil sheets as illustrated in FIGS. 1 and 2, and the slight convergence of their axes 33 produces a slight stepwise misalignment between the successive partition segments 34 in each of the layers as illustrated in FIG. 3, where it is shown that adhesive 37 is effective only in the overlapping juxtaposed end portions of such stepwise aligned partition segments 34.

If a slightly different web negative mask tool such as the one for the underlying foil layer is employed on the under surface of the overlying foil layer, the resulting slanted partition segments 35 may be produced by the etching operation, with a slight converging slant parallel to the desired cell axes 33, as indicated in FIG. 4. This convergent slant partition segment etching operation thus minimizes the stepwise alignment of the successive partition segments making up each partition wall 36, avoiding any risk of total misalignment at the grid corners most remote from focal point F, and thus allows the adhesive 37 to be bonded to all or a larger portion of the facing abutting surfaces of the partition segments 34, all as shown in FIG. 4.

When all of the layers to be assembled or laminated in the cross grid assembly 32 have been dipped in the adhesive bath and withdrawn through the air knife clearing step 68, these web structure sheets are all aligned in careful registration to produce the desired convergent axes 33 for all of the air cell passages 31, utilizing optical or mechanical registration indicia or both impressed on all of the stacked foil webs, and the entire assembly is then secured between clamping surfaces under the clamping pressure desired, 100 pounds, for example, avoiding any unwanted separation of the layers. This allows the assembly in its clamped position to be held at room temperature or to be exposed to curing heat if desired, for the time required to cure the liquid adhesive between the layers. This bonds all of the partition segments in each partition wall to form a solid integral structure, having much greater strength than prior art grids employing sheets of glass as the partition material. When heated clamping plates are employed, they are formed of material, such as selected aluminum alloys, having a coefficient of thermal expansion matching that of the beryllium-copper foil sheets.

The grids of this invention also avoid the disadvantage of interleaved "transparent" material designed to transmit X-rays through the cell passages. Most such materials are incapable of transmitting X-rays without absorbing some portion of the radiation. In this way, the radiation dose to which the patient is exposed can be held to the absolute minimum while achieving high quality mammograms with good detail, excellent contrast and no undesired shadow images of crossed partitions.

If desired, outer dustcover sheets or films of polycarbonate may be applied to protect the exposed surfaces of these air grids.

Diffusion Bonding of Metal Plated Partition Segments

Figure 15:
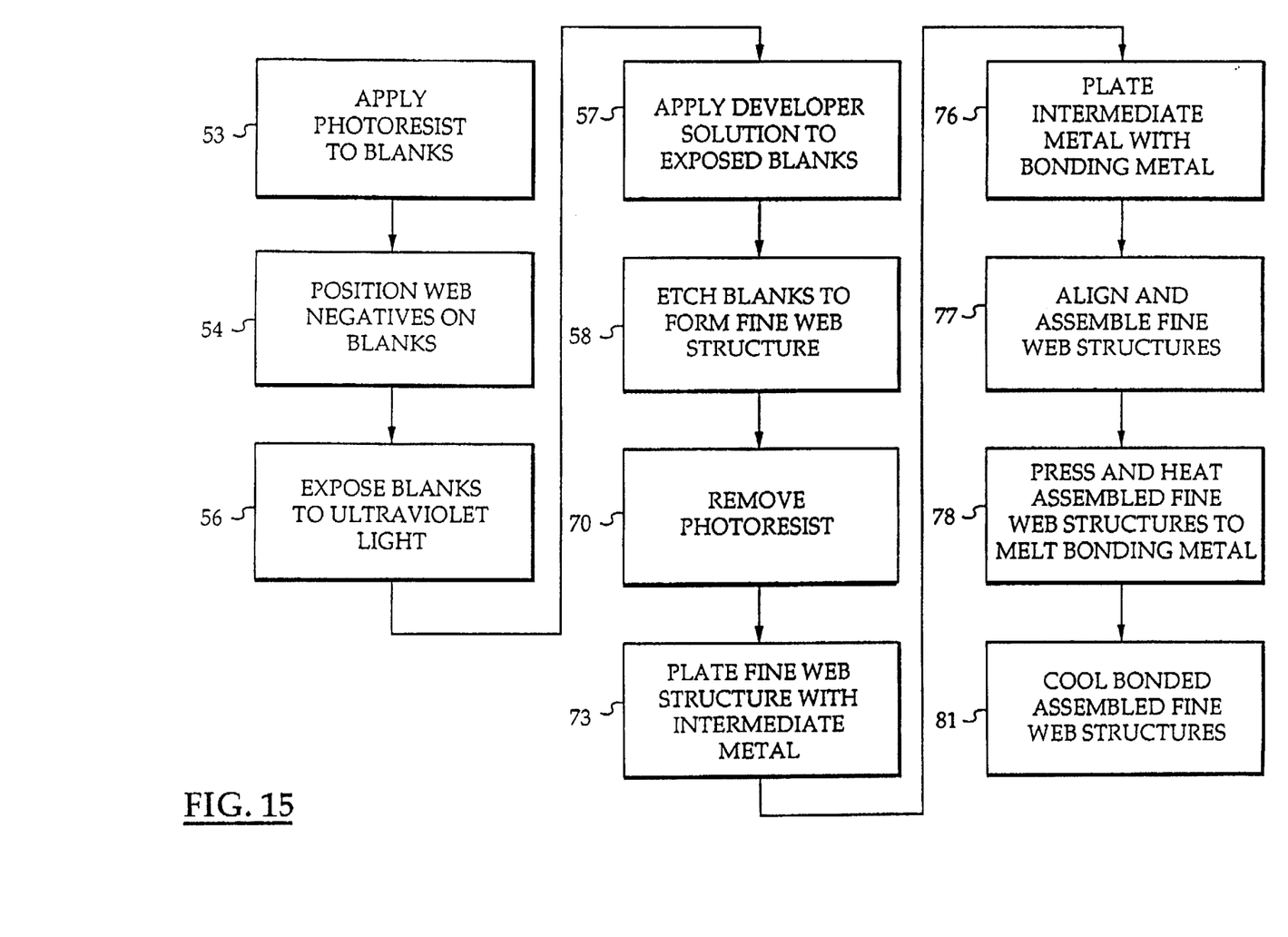
FIG. 15 is a block diagram of a second fabrication method employed to produce air cross grids of this invention incorporating plated metal coatings.

A plated coating of lead or a lead-tin mixture on each photo-etched foil sheet web can be employed, if desired, to enhance the absorption of secondary scattered radiation, and aligned plated partition segments 35 are shown in FIGS. 4 and 4A, and fabricated using the method shown in the flow sheet diagram of FIG. 15.

These plated partition segments 35 are formed of beryllium-copper foil, chemically machined by photo-etching as described above in the converging, slanted segment orientation. After all photoresist is removed in step 70, a coating 72 of intermediate metal, such as copper, is applied by plating to the web's surface, in step 73 (FIG. 15).

An outer bonding metal coating 74 of lead or lead-tin mixture is then plated over coating 72 in step 76. The plated web structures, after being dipped in a liquid flux, are precisely aligned in step 77 using mechanical or optical registration indicia or both marked on each foil sheet, and then clamped in an assembled stack and heated between clamping plates in step 78, in a hydrogen atmosphere in a hydrogen pusher furnace, to a temperature just sufficient to melt and fuse the bonding metal plating layers 74 at the bond zones 79 where the slanted "convergent" partition segments 35 of successive adjacent foil sheets are engaged in coincident alignment (FIGS. 4 and 4A).

After final cooling in step 81, and removal of remaining flux in a vapor de-greasing operation, these plated air cross grids are sturdy, rigid panels, well adapted for use in absorbing secondary scattered radiation in mammography procedures.

It will thus be seen that the objects set forth above, and those made apparent from the preceding description, are efficiently attained and, since certain changes may be made in carrying out the above method and in the construction set forth without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A method for imparting edgewise translation movement to an air cross grid panel having two large pluralities of partition walls extending in substantially transverse respective directions and forming large pluralities of open passages extending through the grid panel, for absorbing scattered secondary radiation in an X-ray mammography exposure procedure, including the steps of:

positioning the grid panel with one plurality of partition walls oriented at an acute angle to the direction of said translation movement, said angle being selected to have a tangent constituting a ratio between two integers, each integer being less than 20;

moving said grid panel in said edgewise translation direction during the entire X-ray exposure at a uniform velocity selected to assure that an integral number of partition walls in both transverse pluralities of walls will pass each point in the image during the entire time of the X-ray exposure.

2. The grid panel translation method defined in claim 1 wherein said angle is also selected to ensure that the path of movement of each grid partition intersection does not coincide with the path of movement of any preceding partition intersections until at least nine partition intersections have moved past each point in the image, whereby repeating trace patterns of partition intersections in the resulting image are minimized.

3. An X-ray grid panel translation method achieving the X-ray exposure time required to produce a mammogram having optimum image quality, comprising the steps of:

making a brief test exposure while measuring the X-ray transmission value of the breast to be imaged, determining from said transmission value the total X-ray exposure time required for optimal imaging, and exposing the patient to X-rays for said total X-ray exposure time so determined while imparting edgewise translation movement at continuous uniform velocity to said grid panel.

4. The grid panel translation method defined in claim 3, wherein the total X-ray exposure time required for optimal imaging is divided into two increments, separated by a pause, with the grid panel translation movement occurring at continuous uniform velocity through each increment of exposure, but with the direction of grid panel movement being reversed during the second increment of exposure, whereby deceleration, stopping and reversed acceleration of the grid panel all occur during the pause between the increments of X-ray exposure.

* * * * *